United States Patent [19]

Godin

[11] 3,979,669

[45] Sept. 7, 1976

[54] PARTICLE ANALYZING SYSTEM

[75] Inventor: Thomas J. Godin, West Hollywood, Fla.

[73] Assignee: Coulter Electronics, Inc., Hialeah, Fla.

[22] Filed: June 24, 1975

[21] Appl. No.: 589,936

Related U.S. Application Data

[63] Continuation-in-part of Ser. No. 400,986, Sept. 26, 1973, Pat. No. 3,902,115.

[52] U.S. Cl. .......................................... 324/71 CP
[51] Int. Cl.² ....................................... G01N 27/00
[58] Field of Search .............. 324/71 CP; 73/432 PS

[56] References Cited
UNITED STATES PATENTS
3,902,115   8/1975   Hogg et al. .................... 324/71 CP

*Primary Examiner*—R. V. Rolinec
*Assistant Examiner*—Vincent J. Sunderdick
*Attorney, Agent, or Firm*—Silverman & Cass, Ltd.

[57] ABSTRACT

A particle analyzing system of the type having an aperture retaining member for obtaining signals from microscopic particles suspended in a fluid which passes through a scanning aperture. The aperture opens on one side thereof to the fluid suspension and on the opposite side to a passageway in the aperture retaining member; the passageway is connected at an entrance end thereof to a source of clean electrolyte and at an exit end thereof to a waste collecting container or isolator and a vacuum source. A vacuum from the source is applied to the collecting container to cause the clean electrolyte to be drawn through the passageway and wash or sweep behind the aperture simultaneously with passage of the suspension through the aperture. A sealed sweep flow isolator drip chamber or tank is interposed in the fluid conduits between the source of clean electrolyte and the passageway with a respective restriction in the fluid conduit on either side of the tank to enable filling of the tank with clean electrolyte to a predetermined desired level below the sealed top of the tank thereby to prevent electrical connection between the electrolyte supply and the passageway.

The waste isolator is provided with a second aperture retaining member disposed in the wall thereof. Sample which has been sensed in the scanning aperture and diluted with the sweep flow clean electrolyte mixed therewith in the passageway is accumulated in the isolator to be tested with low coincidence correction required by passing the same through the second aperture into a secondary isolator. Alternatively, diluted sample present in the fluid conduit between the exit end of the passageway and the waste isolator may itself be forced back through the scanning aperture by applying pressure to the waste isolator; the diluted sample thereby is tested with low coincidence correction required.

17 Claims, 3 Drawing Figures

PARTICLE ANALYZING SYSTEM

CROSS REFERENCE TO RELATED APPLICATION AND PATENTS

This application is a continuation-in-part of a copending application Ser. No. 400,986 filed Sept. 26, 1973, now U.S. Pat. No. 3,902,115, issued Aug. 26, 1975, (herein called "the Parent Patent") for "Self-Cleaning Aperture Tube for Coulter Study Apparatus and Electrolyte Supply System Therefor" filed in the name of the applicant herein along with four others, the structure common to this application and said co-pending application being the joint invention of only the application herein.

The present application also is related in part to the structures disclosed in U.S. Pat. Nos. 3,299,354 and 3,444,464; for purposes of background and detailed description of certain elements referred to herein, these two patents are incorporated herein as a part hereof by specific reference.

One further patent which is related to the subject of the present application is U.S. Pat. No. 3,746,976, now U.S. Reissue Pat. No. 28,558, to which reference also will hereafter be made.

The present application is related also to co-pending application Ser. No. 573,265, filed Apr. 30, 1975, for "Aperture Module" in the name of the applicant herein along with another.

All of the above patents and application are owned by the same assignee as the present application.

BACKGROUND OF THE INVENTION

1. Field of the Invention

This invention relates generally to apparatus for studying the physical properties of particles carried in suspension and more particularly to such apparatus having a novel arrangement for initially filling an isolator tank forming a part of such apparatus with a predetermined desired level of clean electrolyte. The invention also relates to novel method and apparatus for obtaining particle analysis of a diluted sample produced with such apparatus.

2. Description of the Prior Art

The Parent Patent discloses an electrolyte supply system for particle measuring apparatus of the Coulter type in which an aperture retaining member is disposed in communication with a body of particulate liquid suspension to be tested. (The mark "Coulter" is the registered trademark, Registration No. 995,825 of Coulter Electronics, Inc. of Hialeah, Fla.). The aperture retaining member has an aperture to permit passage of the suspension from the body of liquid suspension into the member, and an inlet chamber for introduction of the particle free electrolyte which passes behind the aperture. As described, the structure of the Parent Patent deals with a specific problem which occurred during use of the so-called aperture tube disclosed in U.S. Pat. No. 3,299,354. The structure of U.S. Pat. No. 3,299,354 substantially decreased the possibility of undesirable spurious particle produced signals which sometimes occurred in prior art devices. The aperture tube was self-cleaning in that the suspension in the immediate vicinity of the aperture was kept relatively free of extraneous particles. Despite the self-cleaning aspect of the structure of U.S. Pat. No. 3,299,354, eddy currents of fluid in the aperture tube at the downstream end of the primary bore could occur, and these eddy currents could swirl into the secondary bore immediately adjacent the primary bore.

The structure of U.S. Pat. No. 3,746,976 (U.S. Reissue Pat. No. 28,558) improved on the structure of U.S. Pat. No. 3,299,354 with the addition of a pump device interposed between the first and second chambers of the aperture tube to produce a closed system in which there are no inlets or outlets other than the primary bore in the first chamber. In the structure of the Parent Patent, several configurations of aperture retaining members or tubes are disclosed in which the spurious signal producing zone of the aperture tube continuously is washed simultaneously with passage of the suspension through the aperture such that particles which have been sensed within the aperture and thereafter passed out of the same immediately are swept out of the spurious signal producing zone by particle free liquid which is moved in a passageway behind the aperture and thereafter to an outlet chamber. Application Ser. No. 573,265, entitled "Aperture Module" referred to herein, discloses an improved aperture retaining member incorporating the same wash or sweep flow of clean electrolyte behind the aperture to reduce the occurrence of undesirable spurious signals where they normally are produced.

In the system incorporating each of the aperture tubes of the Parent Patent and the aperture module of application Ser. No. 573,265, an electrolyte supply container or isolator is required to supply the clean electrolyte to wash behind the aperture. The operation of the Coulter device requires that the electrolyte supply chamber be electrically insulated from the aperture retaining member to prevent electrical interference with the particle sensing and measuring performed by the device. In the Parent Patent, the electrolyte supply container is provided with an electrical shield to partially serve this purpose. Additionally, the electrolyte introduced into the container is caused to drip across an air gap and pool at the bottom of the container to prevent completion of an electrical path through the container. It therefore is important that the level of electrolyte in the container initially is established to provide an air gap in the container and that the level does not rise in the container to close the air gap therein to enable completion of an electrical path through the container. It also is important, however, that the electrolyte level in the container does not drop to result in an empty condition thereof in which case maintenance of the important vacuum pressures in the Coulter device would be interrupted. The present invention is intended to provide a novel arrangement of restrictions in the electrolyte supply line on either side of the container to enable initial filling to a proper level of the container with electrolyte.

The microscopic particle sensing method performed with a Coulter device utilizes a particle sensing zone in which more than one particle might be present at any one time and thereby produce a coincidence condition. The particles pass through a minute scanning aperture or sensing zone wherein single particles are detected at a rate often well in excess of one thousand per second. Because of the physical parameters of the scanning aperture and the particle concentration coincidence of two particles in the aperture or zone at the same time or nearly the same time frequently occurs. As a result the effect is that one particle is sensed instead of two, although the amplitude of the resulting signal is proportional to the total of the particle sizes.

One method of correcting for this coincidence of particles simultaneously sensed is to apply a correction which is obtained from a computation using certain predetermined formulae. It is known, however, that the effect of coincidence is a function of concentration of the particles in the suspension to be tested. Decreasing the concentration to a point where coincident passage through the aperture or zone becomes negligible is therefore desirable. The invention also is intended to provide a method and structure whose end is to achieve a high dilution to decrease coincidence.

SUMMARY OF THE INVENTION

The invention provides a particle free electrolyte supply system for electronic particle analyzing apparatus in which an aperture retaining member is positioned in a vessel for containing a body of particulate liquid suspension to be tested. The retaining member has an aperture to permit passage of the suspension from the vessel into the member and a passageway therein for introduction of the electrolyte to pass behind the aperture into the path of the suspension and thereafter into a collection container. A sealed electrolyte supply isolator or container is in fluid communication with the passageway to provide a continuous source of electrolyte therethrough. Electrolyte is introduced to the isolator to drip across an air gap therein and pool at the bottom thereof. Two restrictions are disposed, respectively, upstream and downstream of the isolator to enable filling of the isolator with clean electrolyte to a proper level below the sealed top of the isolator.

The invention further provides method and apparatus for obtaining a diluted particle suspension directly from the collection container providing particle produced signals with negligible coincidence occurring.

DESCRIPTION OF THE PREFERRED EMBODIMENTS

The apparatus with which the system of the invention is intended for use is known as the Coulter electronic particle analyzing device. The Coulter device and its principle of operation are referred to with particularity in U.S. Pat. No. 3,299,354. Inasmuch as this patent is incorporated herein as a part hereof by specific reference, the disclosure thereof will not be repeated except in instances where understanding of the invention herein will be enhanced.

Figure 1:
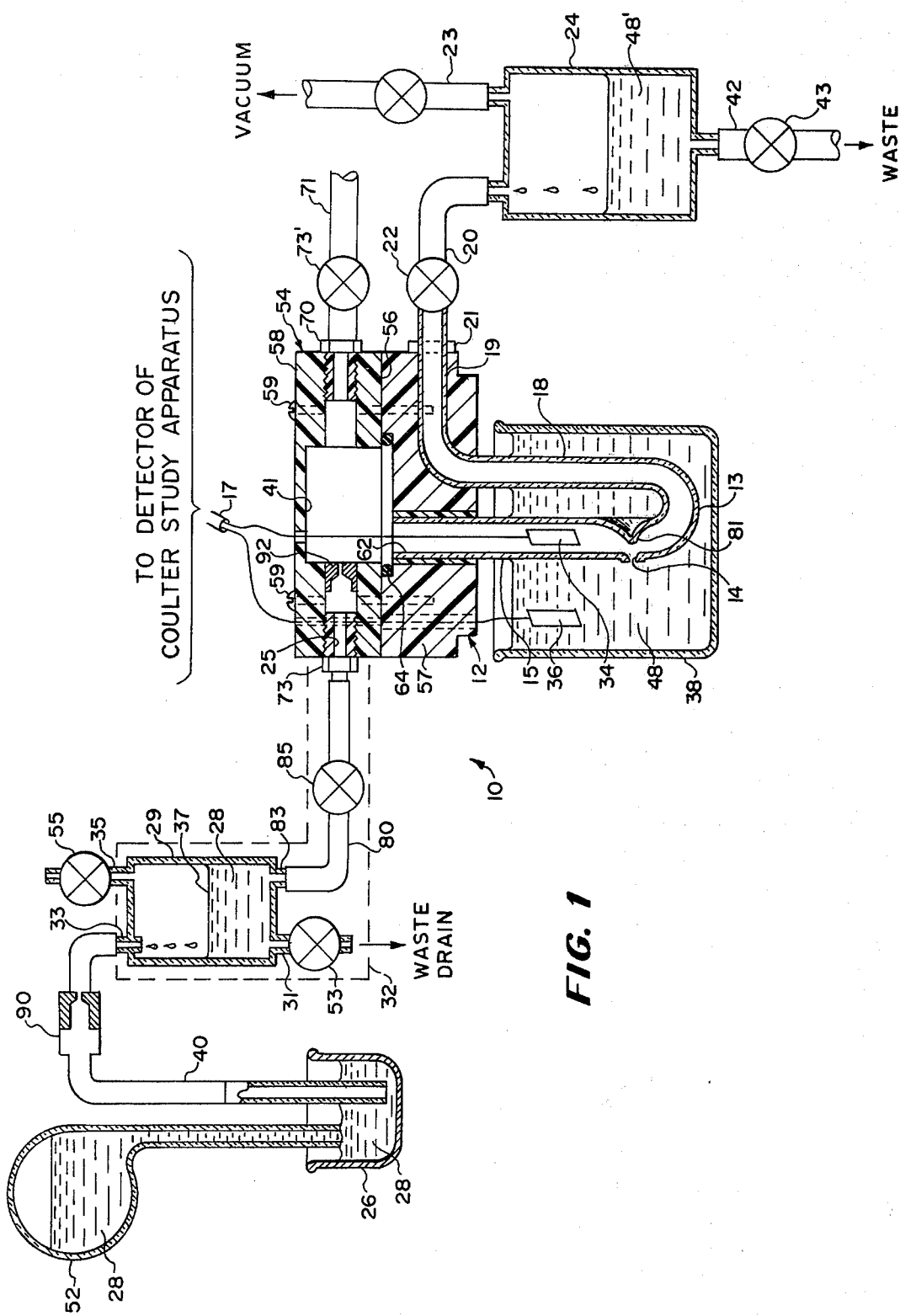
FIG. 1 is a sectional view through a system similar to that of the Parent Patent but illustrating the elements of the present invention, there being partial diagrammatic representation of associated apparatus for the purpose of explaining the same.

Referring to FIG. 1, the system 10 in which the invention is incorporated is shown in connection with common elements thereof illustrated in the Parent Patent. An aperture tube carrying or retaining member 12 is arranged to have a portion thereof comprising the U-shaped tube 13 suspended within a vessel or beaker 38. A measuring or sensing aperture 14 is formed on the side of the U-shaped tube 13 and a generally V-shaped protuberance 81 is formed in the wall of the U-shaped tube 13 opposite the aperture 14 to increase the flow velocity of electrolyte as it passes behind the aperture as described in the Parent Patent and below.

The vessel 38 holds a body of the sample suspension of particles 48 to be drawn through aperture 14; electrodes 34 and 36 are positioned within the U-shaped tube 13 and vessel 38, respectively, and are connected to the detector of a Coulter study apparatus through leads 17 in the manner described in U.S. Pat. No. 3,299,354 for purposes of performing an analysis of the sample suspension.

Aperture tube 13 is associated with the system 10 by mounting the same on coupling block 54 which is separable along the juncture line 56, the two portions 57, 58 of block 54 being secured together by fasteners 59. The tube 13 terminates within the block 54 at its upper end 62 and an O-ring 64 is positioned about the tube to provide an air and liquid-tight seal. The tube is secured by epoxy resin adhesive to the lower half 57 of block 54 to form an easily mounted integral assembly. The tube retaining member 12 thereby may be replaced readily with another retaining member such as an alternate form thereof disclosed in the Parent Patent. Alternately, any suitable aperture module, such as that disclosed in application Ser. No. 573,265, may be used in the system 10. A conduit 71 with valve 73' for flushing and purging the tube 13 and other purposes described below is connected to the tube by fitting 70.

One leg 18 of tube 13 forms the exit portion 19 thereof and terminates at a fitting 21 which couples the terminal portion 19 to a conduit 20. A valve 22 is positioned in conduit 20 and the conduit terminates at a waste drip chamber or isolator 24. A vacuum source (not shown) is connected to isolator 24 by conduit 23. A waste conduit 42 with valve 43 is provided on the bottom of container 24.

Leg 15 forms the entrance portion of tube 13. The upper portion of leg 15 opens to chamber 41 in coupling block 54 which has an inlet port 25 connected by coupling 73 through conduit 80 (having valve 85) to an electrolyte supply drip chamber or isolator 29 having exit port 83. Isolator 29 has a waste drain port 31 and a vent port 35 both of which normally are closed by valves 53, 55, and has a supply port 33. Clean electrolyte 28 is supplied to isolator 29 through supply reservoir 52 which empties into reservoir 26 and is drawn into the isolator through fluid connection 40.

As explained in the Parent Patent, the electrical connection throughout the fluid in system 10 must be broken between reservoir 26 and waste isolator 24 to prevent signal interference with the detector of the Coulter device when the same is in operation. Additionally, it is essential that the level of electrolyte in isolator 29 initially be established and thereafter be maintained constant at a proper level between the top and bottom of the isolator to ensure that there is at all times during operation of the system an unbroken electrical path provided by the electrolyte between the electrodes 34 and 36, and that no air bubbles are present in the system; the presence of air bubbles may cause false signals to be created. For this purpose, each of isolators 29 and 24 is required to function as a drip chamber by introducing liquid thereto in droplet form across an air gap, the resulting electrolyte being accumulated in pools at the bottom of the respective isolators. The pool of electrolyte at the bottom of isolator 29 ensures that the electrical path between electrodes 34, 36 is maintained, so long as the isolator is not evacuated to permit air to enter the system. With respect to waste isolator 24, it is essential only that the level of electrolyte therein does not rise to the top thereof, thus completing electrical connection therethrough. Waste isolator 24 is maintained with an air gap therein by forming the same with a volume capacity greater than that of the fluid to be received therein. When the liquid level in the waste isolator rises too high, valve 43 may be opened to relieve the isolator 24. With respect to supply isolator 29, after initially filling the same to the desired level with particle free liquid, draining it to lower the level thereof would be wasteful and undesirable.

So as initially to fill isolator 29 with electrolyte 28 to a level 37 between the top and bottom of the isolator, a pair of restrictions or chokes 90, 92 is provided in the respective conduits associated with this isolator. Choke 90 is positioned at any point in conduit 40 between reservoir 26 and supply port 33. Choke 92 is positioned at any point in conduit 80 between isolator 29 and aperture retaining member 12. In the illustration of FIG. 1, choke 92 is actually formed within the block 54 but in the path of flow of conduit 80 and upstream of aperture tube 13. This location is for purposes of illustration only and it is to be understood that any other upstream location in conduit 80 would be effective. An electrical shield 32 is provided to shield isolator 29 and the conduit and fittings joining the same to aperture module 12 from stray capacitance coupling to the detector and from picking up extraneous noise and the like.

It is to be understood that the level 37 of electrolyte 28 to be maintained in isolator 29 may be at any location between the top and bottom of the isolator. In the drawings, the level is shown approximately half way between the top and bottom of the isolator but this is for purposes of illustration only. The precise location of the level 37 may be varied by changing the sizes of the chokes 90, 92 and distances therebetween.

In operation, chokes 90, 92 function to establish and maintain level 37 of electrolyte 28 as follows: assuming isolator 29, its associated conduits and chamber 41 are empty at the start of a cycle, valves 85 and 73' are simultaneously opened. Conduit 71 is connected to a source of vacuum (not shown) causing a vacuum to be applied to isolator 29. The vacuum in isolator 29 causes electrolyte 28 to be drawn into the supply conduit 40 at a fairly rapid rate. When the electrolyte reaches choke 90, the flow rate of the electrolyte is substantially reduced. The presence of electrolyte at choke 90 and air at choke 92 causes a vacuum to build up in the isolator 29, because the pressure drop across choke 90 is greater than the drop across choke 92. The vacuum build up in the isolator increases to a level nearly equal to that of the vacuum drawn at conduit 71. Consequently, the flow rate of electrolyte out of the isolator 29 is greater than the flow rate into the isolator causing an increase in vacuum in the isolator. By selecting chokes of proper dimension and lengths and diameter of conduit between the two chokes, as described below, a desired vacuum level in the isolator 29 can be achieved. Valves 73' and 85 are then closed and the residual vacuum remaining in the isolator 29 draws in additional electrolyte until the vacuum is equalized by the weight of the column of electrolyte from the reservoir 26 to the isolator 29 and the level in the isolator rises to that indicated by numeral 37.

Valves 22 and 85 are next opened simultaneously and a vacuum is applied to conduit 23. Vacuum thereby is introduced to waste isolator 24 and through the aperture tube 13 to cause electrolyte 28 to pass through conduit 80 and through the tube. Simultaneously with passage of the electrolyte through the aperture tube, sample solution 48 will be drawn through aperture 14 into the path of the clean electrolyte. The electrolyte passing in the tube behind the aperture increases in velocity by reason of the restriction 81 and creates a sweep or wash flow to move the sensed sample away from the zone in the vicinity of the aperture. The mixture of sample 48 and clean electrolyte 28 moves next through leg 18 of the aperture tube and passes into the waste isolator 24 as diluted sample 48'.

The system maintains the constant level 37 of electrolyte established in isolator 29 during operation because any electrolyte which is drawn from the bottom of the sealed isolator during the sensing procedure is replaced by electrolyte from the supply 26. Thus, as electrolyte is withdrawn from the isolator, a negative pressure (vacuum) is created therein to draw electrolyte into the isolator through supply line 40. Choke 92 restricts the flow of electrolyte to the aperture tube 13 in order to maintain the vacuum draw applied to conduit 23 necessary for continually moving liquid through the aperture tube.

In a working embodiment of the system, the choke sizes, conduit dimensions and vacuum values are as follows:

choke 90 = 0.012 inch diameter
choke 92 = 0.010 inch diameter
diameter of conduits between chokes 90 and 92 = 0.062 inch
length of conduit between chokes 90 and 92 = 12 inches
vacuum draw at conduit 23 = 6 inches Hg.
vacuum draw at conduit 71 = 15 inches Hg.

With these values and dimensions, the level 37 in isolator 29 initially is established approximately mid-way between the top and bottom of the isolator and is there maintained during operation of the system as described. It is to be understood, however, that these values and dimensions may be varied to some degree without adversely affecting the operation of the system. For example, vacuum draw at conduit 71 may be varied to 20 inches Hg. and, although this will move the level 37 to a location other than mid-way between the top and bottom of the isolator 29, operation of the system will remain unchanged. Further, the diameter and length of the conduits and diameter of the chokes may proportionately be varied with equally satisfactory operation of the system. The specific values and dimensions given herein therefore are for purposes of illustration only and are not intended to limit the scope of the invention.

Figure 2:
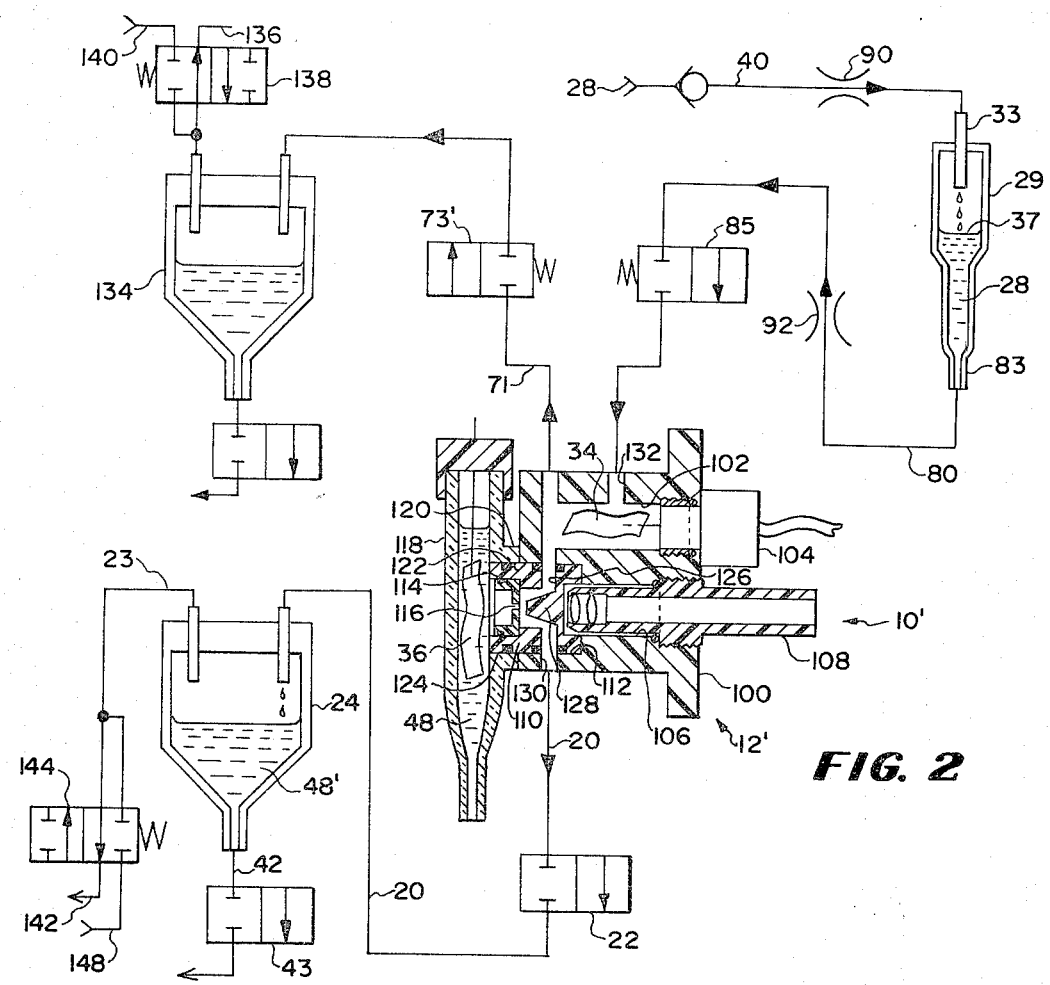
FIG. 2 is a diagrammatic view of the system illustrated in FIG. 1, there being shown in section an alternate aperture retaining member.

FIG. 2 illustrates a system 10' basically similar to that shown in FIG. 1 but with variations and additions. Like elements are identified with the same numerals as in FIG. 1 so only those which are different or additional will be referred to with particularity hereinbelow.

As stated in the earlier description, any suitable aperture module may be used in the system 10. The aperture module 12' shown in the system of FIG. 2 is of the type disclosed in co-pending application Ser. No. 573,265. There is a housing 100 having a chamber 102 with electrode assembly 104 carrying electrode 34 retained therein and a chamber 106 with lens assembly 108 retained therein. Electrode chamber 102 also functions as a bubble trap as described below. An aperture holder 110 is sealingly engaged in a socket 112 coaxial with chamber 106 and a dish-shaped member 114 with aperture 116 is secured in the holder 110. A vessel or bath 118 containing the sample suspension 48 to be analyzed has an electrode 36 suspended therein and the electrodes 34, 36 are connected to the detector of the Coulter study apparatus. The bath 118 has an annular boss 120 for receipt of an extending portion 122 of aperture holder 110 which is sealingly engaged therein by frictional engagement of an O-ring 124. The module 12' has a passageway 126 which opens to chamber 102 and passes behind aperture 116 around a protrusion 128 on a wall of the aperture holder to form a restriction in the passageway immediately behind the aperture. The passageway 126 has an exit port 130 which is connected by suitable conduits and fittings to waste isolator 24.

The particle free electrolyte is supplied to isolator 29 by conduit 40 passing through restriction or choke 90 and drips across an air gap to pool at the bottom thereof. Electrolyte 28 is introduced to aperture module 12' at entrance port 132 which opens to chamber 102. Conduit 80 with restriction or choke 92 and valve 85 joins isolator 29 with module 12'. Conduit 71 also is connected to chamber 102 and joins the same with scavenge isolator 134 with valve 73' interposed therebetween. A vacuum source 136 is introduced to isolator 134 through valve 138 to effect the initial filling operation of isolator 29 as previously described. A pressure source 140 alternately may be introduced to isolator 134 through valve 138 for selectively purging and flushing the aperture module 12' through conduit 71 as may be required. The downstream portion of the system includes conduit 20 connected with waste isolator 24 and valve 22 in the conduit. Diluted sample 48' drips into isolator 24; the valve 43 opens conduit 42 for draining isolator 24 when required. A vacuum source 142 is introduced to isolator 24 through valve 144 for drawing the electrolyte 28 through aperture module 12' during operation of the system. A pressure source 148 alternately may be introduced to isolator 24 through valve 144 to effect flushing of the system. The operation of the system of FIG. 2 is in all respects the same as that of FIG. 1.

As stated, electrode chamber 102 functions as a bubble trap to prevent introduction of air bubbles into the system with the undesirable effects described above. During operation of the system by drawing electrolyte through aperture module 12', the electrolyte is drawn through choke 92. A greater vacuum then exists on the electrolyte on the downstream side of the choke 92 than on the upstream side thereof causing air to be drawn out of solution. This air is trapped in chamber 102 before it can pass through the system. The electrolyte without air bubbles is drawn off the bottom of chamber 102 and into passageway 126 for passage behind the aperture. The air bubbles trapped in chamber 102 can be evacuated therefrom by closing valve 22, opening valves 73' and 85, and applying a vacuum to scavenge isolator 134 at which time the trapped air will be drawn into the scavenge isolator. This, of course, is the same procedure which is followed in initially filling isolator 29 as previously described.

As mentioned in the background herein, during the particle sensing process performed with the systems of FIGS. 1 and 2 in a Coulter device, a certain degree of coincidence of more than one microscopic particle present in the sensing zone occurs for which correction of the data obtained must normally be made. The incidence of coincidence, however, is inversely proportional to the degree of dilution of the sample 48 to be tested. The sample 48 in vessel 38 or bath 118 is of a predetermined dilution and since the volume of electrolyte 28 which passes through aperture retaining members 12, 12' can be metered during operation of the systems 10, 10', the degree of dilution of sample 48' in waste isolator 24 is known. The sample 48' which is of a greater but known dilution than sample 48 therefore may be re-tested and, if the concentration of sample 48' is reduced to a point where coincident passage becomes negligible, the results have high value.

Figure 3:
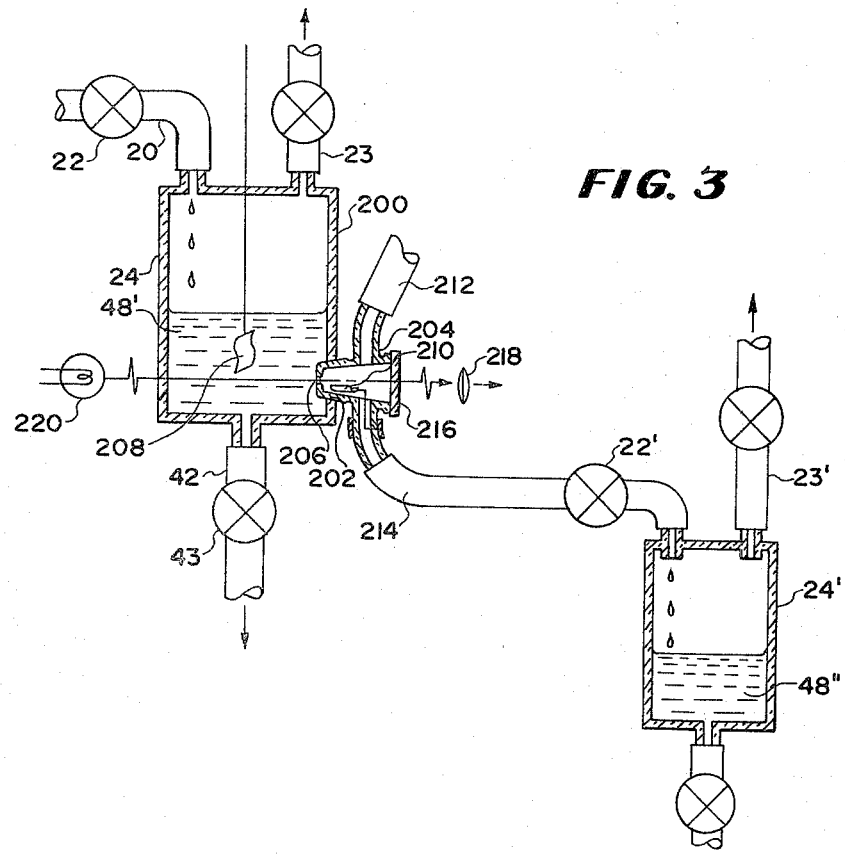
FIG. 3 is a sectional view showing a portion of the system of FIG. 1 illustrating the structure of the invention for obtaining a much-diluted particle suspension from said system.

FIG. 3 illustrates an arrangement for performing analysis of the diluted sample 48' as it is received in waste isolator 24 without any additional processing. For this purpose, wall 200 of isolator 24 is provided with a socket 202 which opens to the sample 48'. An aperture fitting of any convenient construction, for example fitting 204 which is of the type disclosed in U.S. Pat. No. 3,444,464, is positioned within socket 202 such that aperture 206 carried by the fitting opens to the sample 48'. An electrode 208 is suspended in isolator 24 and another electrode 210 is disposed within fitting 204; the electrodes are connected by suitable conductors to the detector of the Coulter study apparatus. An inlet conduit 212 carries particle free electrolyte into and through the fitting 204 to outlet conduit 214 which is connected through valve 22' to secondary waste isolator 24'. Another conduit 23' opens to isolator 24' and a vacuum may be applied thereto to draw electrolyte through conduit 214. Simultaneously, sample 48' will be drawn through aperture 206 to enable the particles thereof to be sensed by the detector of the Coulter device and carried into isolator 24' by the electrolyte introduced through conduit 212. The resultant diluted sample 48'' drips into isolator 24' as previously described. The fitting 204 has an outer cover glass 216 to permit visual examination of the aperture 206 through lens 218 and light source 220.

The degree of concentration of sample 48' is considerably lesser than that of sample 48. In a typical test run, a high concentration of sample 48 might be 6,250:1. Where a 50 micron aperture 14, 116 is in use, the electrolyte sweep flow liquid 28 will dilute the sample 48 entering the aperture by a factor of approximately 16. Thus, the diluted sample 48' entering isolator 24 is about 100,000:1. The sensing process performed on sample 48' with fitting 204 therefore has negligible coincident passage of particles through aperture 206 and consequently correction of the data obtained to account for such coincidence may not be required.

Although analyzing of the much-diluted sample 48' present in waste isolator 24 results in data for which coincidence correction may not be required, the dilution is so great that a considerably longer period of time is required to run the analysis than that required for the sample 48 in order to obtain meaningful data. Further, the sample dilution 48 (6250:1) is predetermined for the purpose of obtaining certain analysis results, for example, red blood cell and platelet count and platelet MCV; a greater dilution may not produce optimal data for these analyses. The sample dilution 48' is useable for obtaining other analysis results, for example, red blood cell MCV and information to enable population distribution of red blood cells. Thus, it is necessary to perform separate analysis operations on different sample dilutions to obtain the various analysis data desired and the system disclosed herein provides a convenient way to achieve this using the dilution 48' produced after the dilution 48 has been analyzed. In the past, this dilution 48' has been discarded as waste after the analyses on dilution 48 have been performed.

Alternatively to use of the structure of FIG. 3 to test sample 48', the same test results of a highly diluted sample can be obtained by forcing sample 48' back through aperture 116, 14 during a rinsing operation thereof. In use of this method, pressure may be introduced to isolator 24 by applying source 148 through valve 144 into conduit 23. During this operation, valve 22 is open and valve 85 is closed. The pressure developed in isolator 24 will cause sample 48' in conduit 20 to flow back into the aperture module 12' (or aperture tube 13) into the sensing zone proximate aperture 116 (or aperture 14). This so-called back-flow or rinse operation will utilize the diluted sample 48' and, if the detector of the Coulter device simultaneously is operated, sensing data will be obtained without the need to adjust the same for coincident passage of particles. This latter procedure is desirable because it utilizes existing elements of the system 10, 10' without the necessity of adding the secondary analyzing elements illustrated in FIG. 3.

Minor variations in the structure and other variations in the arrangement and size of the various parts may occur to those skilled in the art without departing from the spirit or circumventing the scope of the invention as set forth in the appended claims.

What is desired to secure by Letters Patent of the U.S. is:

1. A particle-free electrolyte supply system for particle measuring apparatus in which an aperture retaining member is provided in a vessel for containing a body of particulate liquid suspension to be analyzed, the member having an aperture to permit passage of the suspension from the vessel into the member, the apparatus including a first electrode in the vessel and a second electrode in the member to establish an electrical field in the aperture between the vessel and the member, means including electrical leads connected to the electrodes and adapted to extend connections to a detector to respond to electrical measuring signals produced across the electrodes with passage of particles through said aperture, the member having an inlet chamber for introduction of particle free electrolyte, an outlet chamber in fluid communication with the inlet chamber, an electrolyte isolator and first conduit for fluid communication between the isolator and inlet chamber, an electrolyte supply and second conduit for fluid communication between the supply and isolator, a waste container in fluid communication with the outlet chamber, and fluid moving means connected to the waste container, said system comprising, a first restriction in the first conduit and a second restriction in the second conduit, whereby the fluid moving means will cause the electrolyte to pass from the supply to the isolator but the volume of electrolyte in the isolator will be established and maintained constant.

2. A system as claimed in claim 1 in which the isolator is a drip container and the electrolyte drips across an air gap therein to pool at the bottom thereof, but the level of electrolyte in the container is maintained constant.

3. A system as claimed in claim 1 in which the restrictions are chokes and the relationship between the first choke to the second choke is 0.012:0.016.

4. A system as claimed in claim 1 in which the electrolyte and the tested suspension form a dilution accumulated in the waste container, said waste container having means provided in a wall thereof to sense particles in the dilution electrically and thereafter to pass same to a secondary container.

5. A system as claimed in claim 4 in which said last named means include a socket in the wall and an aperture retaining fitting engaged in said socket.

6. A system as claimed in claim 1 in which the electrolyte and the analyzed suspension form a dilution accumulated in the waste container, and means associated with the waste container to return the dilution back through the aperture to analyze the dilution.

7. A system as claimed in claim 6 in which said last named means include a pressure source coupled with said waste container.

8. A system as claimed in claim 7 in which the waste container and outlet chamber are connected by a conduit defining a volume of said dilution and said volume is returned through the aperture upon application of pressure by said pressure source.

9. A particle analyzing system for analyzing microscopic particles in a suspension, the system comprising, a vessel for containing a body of the suspension, an aperture retaining member provided in the vessel, the member having an aperture to permit passage of the suspension from the vessel into the member, a first electrode in the vessel and a second electrode in the member to establish an electrical field in the aperture between the vessel and the member, means including electrical leads connected to the electrodes and adapted to extend connections to a detector to respond to electrical measuring signals produced across the electrodes with passage of the particles through said aperture, the member having an inlet chamber for introduction of particle free electrolyte into the path of the suspension to mix therewith and form a dilution, an outlet chamber in fluid communication with the inlet chamber to receive the dilution, a waste container in fluid communication with the outlet chamber, and fluid moving means connected to the waste container to move the dilution into the waste container to be accumulated therein, the waste container having means provided in a wall thereof to analyze the dilution a second time and thereafter to convey the same to a secondary container.

10. A system as claimed in claim 9 in which said last named means include a socket in the wall and an aperture retaining fitting engaged in said socket.

11. A particle analyzing system for analyzing microscopic particles in a suspension, the system comprising, a vessel for containing a body of the suspension, an aperture retaining member provided in the vessel, the member having an aperture to permit passage of the suspension from the vessel into the member, a first electrode in the vessel and a second electrode in the member to establish an electrical field in the aperture between the vessel and the member, means including electrical leads connected to the electrodes and adapted to extend connections to a detector to respond to electrical measuring signals produced across the electrodes with passage of the particles through said aperture, the member having an inlet chamber for introduction of particle free electrolyte into the path of the suspension to mix therewith and form a dilution, an outlet chamber in fluid communication with the inlet chamber to receive the dilution, a waste container in fluid communication with the outlet chamber, and fluid moving means connected to the waste container to move the dilution into the waste container to be accumulated therein, the waste container having means associated therewith to return the dilution back through the aperture to analyze the dilution.

12. A system as claimed in claim 11 in which said last named means include a pressure source coupled with said waste container.

13. A system as claimed in claim 12 in which the waste container and outlet chamber are connected by a conduit defining a volume of said dilution and said volume is returned through the aperture upon application of pressure by said pressure source.

14. A method for analyzing microscopic particles in a particle analyzing device including a vessel for containing the particles in a body of suspension, an aperture retaining member provided in the vessel and the member having an aperture to permit passage of the suspension from the vessel into the member, a first electrode in the vessel and a second electrode in the member to establish an electrical field in the aperture between the vessel and the member, means including electrical leads connected to the electrodes and adapted to extend connections to a detector to respond to electrical measuring signals produced across the electrodes with passage of the particles through said aperture, the member having in inlet chamber and an outlet chamber in fluid communication with the inlet chamber, a sweep-flow container for retaining particle free electrolyte in fluid communication with the inlet chamber, and a waste container in fluid communication with the outlet chamber, said method comprising the steps of:

moving the electrolyte from the sweep-flow container into the inlet chamber and simultaneously moving the suspension through the aperture to mix with the electrolyte to form a dilution, accumulating the dilution in the waste container, and returning the dilution back through the aperture to analyze the particles in the dilution.

15. A method as claimed in claim 14 in which the step of moving is performed by applying a vacuum to the waste container.

16. A method as claimed in claim 14 in which the step of returning is performed by applying pressure to the waste container from the exterior thereof.

17. A method as claimed in claim 14 in which the waste container and outlet chamber are connected by a conduit defining a volume of said dilution and the step of returning is performed by returning said volume back through the aperture.

* * * * *